(12) United States Patent
Claussen et al.

(10) Patent No.: US 12,138,323 B2
(45) Date of Patent: Nov. 12, 2024

(54) INITIATOR SYSTEM WITH POLYMERIZABLE THIOUREA COMPONENT, DENTAL COMPOSITION AND USE THEREOF

(71) Applicant: Solventum Intellectual Properties Company, Maplewood, MN (US)

(72) Inventors: Kai U. Claussen, Duesseldorf (DE); Johannes M. Leykauff, Weilheim (DE); Wolf Steiger, Weil-Petzenhausen (DE); Peter Bissinger, Diessen (DE)

(73) Assignee: Solventum Intellectual Properties Company, Maplewood, MN (US)

(*) Notice: Subject to any disclaimer, the term of this patent is extended or adjusted under 35 U.S.C. 154(b) by 0 days.

(21) Appl. No.: 18/556,708

(22) PCT Filed: Mar. 28, 2022

(86) PCT No.: PCT/IB2022/052845
§ 371 (c)(1),
(2) Date: Oct. 23, 2023

(87) PCT Pub. No.: WO2022/229734
PCT Pub. Date: Nov. 3, 2022

(65) Prior Publication Data
US 2024/0189196 A1    Jun. 13, 2024

(30) Foreign Application Priority Data
Apr. 29, 2021   (EP) .................................... 21171076

(51) Int. Cl.
| A61K 6/61 | (2020.01) |
| A61K 6/30 | (2020.01) |
| A61K 6/887 | (2020.01) |

(52) U.S. Cl.
CPC .................. *A61K 6/61* (2020.01); *A61K 6/30* (2020.01); *A61K 6/887* (2020.01)

(58) Field of Classification Search
CPC ....................................................... A61K 6/61
See application file for complete search history.

(56) References Cited

U.S. PATENT DOCUMENTS

| 4,209,434 A | 6/1980 | Wilson et al. |
| 4,360,605 A | 11/1982 | Schmitt et al. |
| 4,642,126 A | 2/1987 | Zador et al. |
| 4,652,274 A | 3/1987 | Boettcher et al. |
| 4,737,593 A | 4/1988 | Ellrich et al. |
| 5,154,762 A | 10/1992 | Mitra et al. |
| 5,918,772 A | 7/1999 | Keller et al. |
| 5,944,419 A | 8/1999 | Streiff |
| 6,444,725 B1 | 9/2002 | Trom et al. |
| 7,173,074 B2 | 2/2007 | Mitra et al. |
| 8,651,867 B2 | 2/2014 | Zilberman |
| 9,408,781 B2 | 8/2016 | Qian et al. |
| 2003/0166740 A1 | 9/2003 | Mitra et al. |
| 2004/0235981 A1 | 11/2004 | Qian |
| 2006/0187752 A1 | 8/2006 | Keller |
| 2007/0040151 A1 | 2/2007 | Utterodt et al. |
| 2007/0088096 A1 | 4/2007 | Mitra et al. |
| 2007/0090079 A1 | 4/2007 | Kelller |
| 2007/0196792 A1 | 8/2007 | Johnson et al. |
| 2007/0254998 A1 | 11/2007 | Orlowski et al. |
| 2015/0238291 A1 | 8/2015 | Hauptmann et al. |
| 2016/0051450 A1 | 2/2016 | Kashiki et al. |
| 2017/0020639 A1 | 1/2017 | Jahns et al. |
| 2017/0296442 A1 | 10/2017 | Renn et al. |
| 2020/0253834 A1* | 8/2020 | Moszner .................. A61K 6/79 |

FOREIGN PATENT DOCUMENTS

| EP | 0235826 B1 | 4/1990 |
| WO | 2005016783 A1 | 2/2005 |
| WO | 2007098485 A2 | 8/2007 |
| WO | 2007104037 A2 | 9/2007 |
| WO | 2008033758 A2 | 3/2008 |
| WO | 2009061884 A1 | 5/2009 |
| WO | 2010123800 A1 | 10/2010 |
| WO | 2015073246 A1 | 5/2015 |
| WO | 2018102484 A1 | 6/2018 |
| WO | 2018187375 A1 | 10/2018 |

OTHER PUBLICATIONS

International Search Report for PCT International Application No. PCT/IB2022/052845, mailed on Jun. 14, 2022, 3 pages.

* cited by examiner

*Primary Examiner* — Michael F Pepitone

(57) ABSTRACT

The invention relates to an initiator system for curing a dental composition, the initiator system comprising a hydroperoxide component, a transition metal component, a polymerizable thiourea component, the polymerizable thiourea component comprising a thiourea moiety which is attached to a (meth)acrylate moiety through a $C_{3-11}$ alkyl chain. The invention also relates to a dental composition comprising such an initiator system, and curable components, in particular curable components comprising acidic moieties.

13 Claims, No Drawings

INITIATOR SYSTEM WITH POLYMERIZABLE THIOUREA COMPONENT, DENTAL COMPOSITION AND USE THEREOF

CROSS REFERENCE TO RELATED APPLICATIONS

This application is a national stage filing under 35 U.S.C. 371 of PCT/IB2022/052845, filed Mar. 28, 2022, which claims the benefit of European Application No. 21171076.9, filed Apr. 29, 2021, the disclosures of which are incorporated by reference in their entireties herein.

FIELD OF THE INVENTION

The invention relates to an initiator system comprising a polymerizable thiourea component and an oxidizing agent. The initiator system is useful for curing curable compositions comprising curable components with acidic moieties, in particular in the dental field.

BACKGROUND

For curing polymerizable compositions different initiator systems are known, including photo-initiator system and redox-initiator systems.

Depending on the further components of the polymerizable composition, a suitable initiator system has to be selected as not all initiator systems show the same performance.

In particular, the curing of polymerizable compositions comprising acidic components is often challenging.

For curing these kinds of compositions an initiator system comprising a peroxide component, a thiourea component and an accelerator component has been proposed.

E.g. US2016/0051450A1 (Kashiki et al.) relates to a curable composition comprising: a radical polymerizable monomer having no acidic group; a hydroperoxide compound; and at least one cyclic thiourea compound selected from the group consisting of a substituted ethylene thiourea compound, a substituted propylene thiourea compound, and a substituted butylene thiourea compound (a3-3).

US2004/235981A1 (Quian) describes dental composition comprising (a) at least one acidic compound; (b) at least one polymerizable monomer without any acidic group where the polymerizable group is selected from the group consisting of an acrylate, a methacrylate and a vinyl group; (c) a substituted thiourea selected from the group consisting of 1-(2-pyridyl)-2-thiourea and 1-(2-tetrahydrofurfuryl)-2-thiourea; and (d) a hydroperoxide compound with at least one hydroperoxide group attached to a tertiary carbon; the composition being a shelf-stable two-part self-adhering composition.

US2003/166740A1 (Mitra et al.) and US 2007/880% A1 (Mitra et al.) describe a hardenable composition that includes polymerizable urea or thiourea compounds that function as reductants in redox polymerization reactions. Preferred are polymerizable thiourea reducing agents that include an allyl group and a (meth)acrylate group. These components are said to be advantageous as they can reduce the potential toxic or narcotic properties of derivatives from urea or thiourea compounds.

US2007/0040151A1 (Utterodt et al.) relates to a two-component initiator system comprising (a) a hydroperoxide compound containing one or more hydroperoxide groups that are bound to a tertiary carbon, (b) a thiourea derivative, particularly an acetyl thiourea; and (c) as accelerator a soluble copper compound.

However, there is still room for improvement especially with regard to the requirements to be fulfilled with respect to modern dental materials.

DESCRIPTION OF THE INVENTION

Resin modified glass ionomer cements (RMGICs) merge the chemistry of traditional glass ionomer with elements of more sophisticated resin cements. Thus, RMGICs offer benefits of both cement categories, e.g. higher fluoride release than pure resin cements and better mechanics than pure glass ionomer cements.

RMGICs can be used to cement dental restoration made of strong materials to retentive tooth preparations. However, compared to dental resin cements the adhesive bond strength of RMGICs to dentin is rather low due to its glass ionomer cement heritage and the lack of adhesive monomers.

Thiourea compounds usually work well in RMGIC formulations but they often do not provide adequate bond strength to dentin.

Thus, there is a need for an initiator system which can be used for curing a polymerizable composition containing acidic components effectively.

The initiator system should finally result in a sufficient or even improved bond strength of the cured composition to dentin without negatively affecting the curing conditions, e.g. setting time.

The initiator system should also be working in an environment containing water, e.g. suitable for curing resin modified glass ionomer cements (RMGICs).

It would also be desirable to have an initiator system which is acceptable from a toxicological aspect.

If possible, the initiator system should have good wetting properties to the hydrophilic dentin surface and/or should have better miscibility with the hydrophobic components of the curable composition to be cured.

One or more of the above objects are addressed by the invention described in the present text and claims.

In one embodiment the invention features an initiator system comprising a hydroperoxide component, a transition metal component comprising in particular comprising ions of Cu, Ti, V, Cr, Mn, Fe, Co, Ni, Zn or mixtures thereof, a polymerizable thiourea component, the polymerizable thiourea component comprising a thiourea moiety which is attached to a (meth)acrylate moiety through a $C_{3-11}$ alkyl chain as described in the present text and claims.

In a further embodiment the invention features a dental composition comprising the initiator system, curable components, in particular curable components comprising acidic moieties, optionally filler, optionally additive(s) as described in the present text and claims.

The invention is also related to a kit of parts comprising the dental composition as described in the present text and claims and the following parts alone or in combination: dental milling block; dental crown; mixing tips; dental adhesive; dental conditioner.

Moreover, the invention features a method of using the initiator system described in the present text and claims for curing a curable composition comprising curable components comprising acidic moieties.

Unless defined differently, for this description the following terms shall have the given meaning:

The term "compound" or "component" is a chemical substance which has a certain molecular identity or is made of a mixture of such substances, e.g., polymeric substances.

A "hardenable or curable or polymerizable component" is any component which can be cured or solidified in the presence of a photo-initiator by radiation-induced polymerization. A hardenable component may contain only one, two, three or more polymerizable groups. Typical examples of polymerizable groups include unsaturated carbon groups, such as a vinyl group being present i.a. in a (methyl)acrylate group.

As used herein, "(meth)acryl" is a shorthand term referring to "acryl" and/or "methacryl". For example, a "(meth) acryloxy" group is a shorthand term referring to either an acryloxy group (i.e., $CH_2=CH-C(O)-O-$) and/or a methacryloxy group (i.e., $CH_2=C(CH_3)-C(O)-O-$).

As used herein, "hardening" or "curing" a composition are used interchangeably and refer to polymerization and/or crosslinking reactions including, for example, photo-polymerization reactions and chemical-polymerization techniques (e.g., ionic reactions or chemical reactions forming radicals effective to polymerize ethylenically unsaturated compounds) involving one or more materials included in the composition.

An "initiator" is a substance being able to start or initiate the curing process of polymerizable components or monomers, e.g. redox/auto-cure chemical reaction or by a radiation induced reaction or by a heat induced reaction.

A "redox initiator system" is defined as the combination of reducing agent(s) and oxidizing agent(s) being located on the application part of the application device. If present, transition metal component(s) are also regarded as components of the redox initiator system.

"Dental article" means an article which is to be used in the dental field, especially as or for producing a dental restoration. A dental article has typically two different surface portions, an outer surface and an inner surface. The outer surface is the surface which is typically not in permanent contact with the surface of a tooth. In contrast thereto, the inner surface is the surface which is used for attaching or fixing the dental article to a tooth. If the dental article has the shape of a dental crown, the inner surface has typically a concave shape, whereas the outer surface has typically a convex shape. A dental article should not contain components which are detrimental to the patient's health and thus free of hazardous and toxic components being able to migrate out of the dental or orthodontic article.

"Dental restoration" means dental articles which are used for restoring a tooth to be treated. Examples of dental restorations include crowns, bridges, inlays, onlays, veneers, facings, copings, crown and bridged framework, and parts thereof.

A "particle" means a substance being a solid having a shape which can be geometrically determined. The shape can be regular or irregular. Particles can typically be analysed with respect to e.g. particle size and particle size distribution.

The particle size (d50) of a powder can be obtained from the cumulative curve of the grain size distribution. Respective measurements can be done using commercially available granulometers (e.g. Malvern Mastersizer 2000). "D" represents the diameter of powder particles and "50" refers to the volume percentage of the particles. Sometimes, the 50% is also expressed as "0.5". For example, "(d50)=1 µm" means that 50% of the particles have a size of 1 µm or less.

"Paste" shall mean a soft, viscous mass of solids dispersed in a liquid.

"Viscous" means a viscosity above 50 Pa*s (at 23° C.).

A "liquid" means any solvent or liquid being able to at least partially disperse or dissolve a component at ambient conditions (e.g. 23° C.). A liquid typically has a viscosity below 10 or below 8 or below 6 Pa*s.

"Glass ionomer cement" (GIC) means a cement which cures or hardens by the reaction of an acid-reactive glass and a polyacid in the presence of water.

"Resin-modified glass ionomer cement" or "RMGIC" shall mean a GIC containing in addition polymerizable component(s), an initiator system and typically a diluting agent such as 2-hydroxy-ethyl-methacrylate (HEMA).

"Acid-reactive filler" shall mean a filler that chemically reacts in the presence of a (poly)acid leading to a hardening reaction, e.g. glass-ionomer cement reaction.

"Non acid-reactive filler": shall mean a filler, which does not show a chemical hardening reaction within about 30 min, if mixed with a (poly)acid at ambient conditions (e.g. 23° C.).

To distinguish an acid-reactive filler from a non acid-reactive filler the following test can or is to be conducted: A composition is prepared by mixing Part A with Part B in a mass ratio of 3 to 1, wherein: Part A contains: filler to be analysed: 100 wt. %; Part B contains: poly (acrylic acid co maleic acid) (Mw: about 20,000+/−3,000): 43.6 wt. %, water: 47.2 wt. %, tartaric acid: 9.1 wt. %, benzoic acid: 0.1 wt. %.

"Polyacid" or "polyalkenoic acid" shall mean a polymer having a plurality of acidic repeating units (e.g. more than 10 or more than 20 or more than 50). That is, the acidic repeating units are attached to or pending from the backbone of the polymer.

A "storage stable composition" is a composition which can be stored for an adequate period of time (e.g. at least 12 months under ambient conditions or 3 months under accelerated aging conditions) without showing significant performance issues (e.g. reduced mechanical properties or undesired setting behaviours).

As used herein, a "dental surface" refers to tooth structures (e.g., enamel, dentin, and cementum) and bone.

"Ambient conditions" mean the conditions which the composition described in the present text is usually subjected to during storage and handling. Ambient conditions may, for example, be a pressure of 900 to 1,100 mbar, a temperature of 10 to 40° C. and a relative humidity of 10 to 100%. In the laboratory ambient conditions are typically adjusted to 20 to 25° C. and 1,000 to 1,025 mbar (at maritime level).

As used herein, "a", "an", "the", "at least one" and "one or more" are used interchangeably. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about".

The terms "comprise" or "contain" and variations thereof do not have a limiting meaning where these terms appear in the description and claims. "Consisting essentially of"

means that specific further components can be present, namely those which do not materially affect the essential characteristic of the article or composition. "Consisting of" means that no further components should be present. The term "comprise" shall include also the terms "consist essentially of" and "consists of".

A composition is "essentially or substantially free of" a certain component, if the composition does not contain said component as an essential feature. Thus, said component is not willfully added to the composition either as such or in combination with other components or ingredient of other components. A composition being essentially free of a certain component usually does not contain that component at all. However, sometimes the presence of a small amount of the said component is not avoidable e.g. due to impurities contained in the raw materials used.

DETAILED DESCRIPTION

It has been found that the invention described in the text provides a couple of advantages.

The initiator system described in the present text provides a suitable alternative to existing initiator systems containing thiourea components as reducing agents.

The initiator system is also able to work in an aqueous environment.

The initiator system is in particular suitable for curing a resin-modified glass ionomer composition.

Due to the presence of the (meth)acrylate group, the polymerizable thiourea component can also be co-polymerized with other polymerizable components present in a curable composition.

This property can be beneficial in that it may help to avoid an undesired migration or leaching out of the thiourea component from the curable composition during use.

Further, due to its structure comprising a rather hydrophilic thiourea moiety and a rather hydrophobic (meth)acrylate moiety the polymerizable thiourea component is amphiphilic and has well-balanced surface-active properties.

It was also found that the initiator system is suitable to improve the bond strength of a curable composition to hard dental tissue, in particular dentin.

The initiator system comprises a polymerizable thiourea component.

The polymerizable thiourea component comprises a thiourea moiety which is attached to a (meth)acrylate moiety through a spacer unit comprising an alkyl chain, preferably a $C_{3-11}$ alkyl chain.

The polymerizable thiourea component functions as reducing agent in a redox-initiator system.

The molecular weight of the polymerizable thiourea component is typically in a range of 200 to 400 g/mol. This molecular weight range seems to be a good compromise to allow a sufficient molecular mobility and reactivity within a curable composition to be cured.

The polymerizable thiourea component typically has the general formula:

MA-S-TU-R with
MA: (meth)acrylate,
S: $C_{3-11}$ linear alkyl, or $C_{3-8}$ linear alkyl or $C_{3-6}$ linear alkyl,
TU: thiourea,
R: $C_1$ to $C_6$ alkyl or cyclo alkyl ($C_{3-6}$, preferably $C_{5-6}$).

The polymerizable thiourea component does typically not comprise an allyl moiety ($H_2C=CH-CH_2-$), and a carbamate moiety ($-O-CO-NH-$).

Suitable polymerizable thiourea component typically show an average water-contact angle in the range of more than 10° or 15° determined over a time period of 0 to 12 s after placement of a water droplet on a surface coated with the polymerizable thiourea component.

Preferred polymerizable thiourea components include N-(5-methacryloxypentyl)-N'-ethyl thiourea, N-(5-methacryloxypentyl)-N'-cyclohexyl thiourea, N-(5-methacryloxyundecyl)-N'-ethyl thiourea and mixtures thereof.

The polymerizable thiourea component is typically present in the following amount(s): at least 0.1 or 0.2 or 0.3 wt. %; utmost 3 or 2.5 or 2 wt. %; range: 0.1 to 3 or 0.2 to 2.5 or 0.3 to 2 wt. %; wt. % with respect to the amount of the curable composition to be cured.

The initiator system comprises a hydroperoxide component.

The hydroperoxide component has one or more hydroperoxide groups (—OOH groups) per molecule, and more preferably a hydroperoxide having a —OOH group bonded to a tertiary carbon atom per molecule.

Specific examples of hydroperoxide components which can be used include tetramethylbutyl hydroperoxide, t-butyl hydroperoxide, t-amylhydroperoxide, cumene hydroperoxide, p-menthane hydroperoxide, p-isopropylcumyl hydroperoxide, diisopropylbenzene hydroperoxide, and diisopropyl-benzene dihydroperoxide, benzene hydroperoxide, pinane hydroperoxide, 5-phenyl-4-pentenylhydroperoxide, p-diisopropylbenzene hydroperoxide, and mixtures thereof, wherein cumene hydroperoxide and/or 1,1,3,3-tetramethyl-butyl hydroperoxide are sometimes preferred.

One or more hydroperoxide components can be used, if desired.

The hydroperoxide component is typically present in the following amount(s): at least 0.1 or at least 0.2 or at least 0.3 wt. %; utmost 5 or utmost 4 or utmost 3 wt. %; range: 0.1 to 5 or 0.2 to 4 or 0.3 to 3 wt. %; wt. % with respect to the amount of the curable composition to be cured.

The ratio of the hydroperoxide component to the polymerizable thiourea component is typically in a range of 5/1 to 1/2 with respect to ratio of the hydroperoxide moiety and the thiourea moiety, in particular in a range of 3/1 to 1/2 or 3/1 to 1/1.

Using such a ratio has been found to be advantageous as it allows the setting of a curable composition in an adequate time frame, e.g. within about 10 mins.

It was found that the setting of a curable composition in an adequate time frame can be achieved even better, if the hydroperoxide component is used in equal amount or in excess over to the amount of the polymerizable thiourea component (calculated with respect to the mol equivalents of the functional moieties of hydroperoxide and thiourea).

Suitable transition metal component(s) include organic and/or inorganic salt(s) selected from titanium, vanadium, chromium, manganese, iron, cobalt, nickel, copper and/or zinc, with copper, vanadium and iron being sometimes preferred.

Useful salts include acetate(s), chloride(s), sulphate(s), benzoate(s), acetylacetonate(s), naphthenate(s), carboxylate(s), bis(1-phenylpentan-1,3-dione) complexes, salicylate(s), complexes with ethylenediaminetetraacetic acid of either of the transition metals and mixtures thereof.

According to one embodiment, the transition metal component is in an oxidation stage, which allows the component to be reduced. Useful oxidation stages include +2, +3, +4, +5, +6 and +7, as applicable.

Copper component(s) are sometimes preferred. The oxidation stage of copper in the copper component(s) is preferably +1 or +2.

Typical examples of copper component(s) which can be used include salts and complexes of copper including copper acetate, copper chloride, copper benzoate, copper acetylacetonate, copper naphthenate, copper carboxylates, copper bis(1-phenylpentan-1,3-dione) complex (copper procetonate), copper salicylate, complexes of copper with thiourea, ethylenediaminetetraacetic acid and/or mixtures thereof. The copper compounds can be used in hydrated form or free of water. Especially preferred is copper acetate.

The amount of transition metal component which can be used is not particularly limited. The transition metal salt should be used in an amount sufficient to achieve the intended purpose.

If present, the transition metal component(s) is typically present in the following amounts: at least 0.00001 wt. % or at least 0.0001 wt. % or at least 0.001 wt. %; utmost 1.5 wt. % or utmost 1.0 wt. % or utmost 0.5 wt. %; range: 0.00001 wt. % to 1.5 wt. % or 0.0001 wt. % to 1.0 wt. % or 0.001 wt. % to 0.5 wt. %; wt. % with respect to the amount of the curable composition to be cured.

The initiator system may also comprise a stabilizer component.

Suitable stabilizers include free radical scavengers such as substituted and/or unsubstituted hydroxyaromatics, e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, 2-(2'-hydroxy-5'-methacryloxyethylphenyl)-2H-benzotriazole, and phenothiazine.

Besides the above components, the following stabilizers were found to be useful: stabilizer component(s) comprising a free-radical moiety, including 2,2-diphenyl-1-picrylhydrazyl, 4-hydroxy-2,2,6,6-tetramethyl-piperidine 1-oxyl, 2,2,6,6-Tetramethyl-piperidinyloxyl, 2,6-di-tert-butyl-alpha-(3,5-di-tert-butyl-4-oxo-2,5-cyclohexadien-1-ylidene)-p-tolyloxyl, triphenylmethyl radical, and mixtures thereof.

If present, stabilizer component(s) are typically present in the following amount(s): at least 0.005 or at least 0.01 or at least 0.02 wt. %; utmost 0.3 or utmost 0.2 or utmost 0.1 wt. %; range: 0.005 to 0.3 or 0.01 to 0.2 or 0.02 to 0.1 wt. %; wt. % with respect to the amount of the curable composition to be cured.

According to certain embodiments, the dental composition further comprises a photo-initiator or photo-initiator system.

As photo-initiator(s), those which can polymerize the polymerizable monomer(s) by the action of visible light having a wavelength of in the range of 350 nm to 500 nm are preferred.

Suitable photo-initiator(s) often contain an alpha di-keto moiety, an anthraquinone moiety, a thioxanthone moiety or benzoin moiety.

Examples of photo-initiator(s) include camphor quinone, 1-phenyl propane-1,2-dione, benzil, diacetyl, benzyl dimethyl ketal, benzyl diethyl ketal, benzyl di(2-methoxyethyl) ketal, 4,4,'-di-methylbenzyl dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropyl thioxanthone, 2-nitrothioxanthone, 2-methyl thioxanthone, 2,4-dimethyl thioxanthone, 2,4-diethyl thioxanthone, 2,4-diisopropyl thioxanthone, 2-chloro-7-trifluoromethyl thioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethyl-aminophenyl)ketone, 4,4,'-bisdiethylaminobenzophenone.

Using acylphosphine oxides was found to be useful, as well.

Suitable acylphosphine oxides can be characterized by the following formula

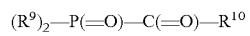

wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S-, O-, or N-containing five- or six-membered heterocyclic group, or a —Z—C(=O)—P(=O)—$(R^9)_2$ group, wherein Z represents a divalent hydrocarbyl group such as alkylene or phenylene having 2 to 6 carbon atoms.

Suitable systems are also described e.g. in U.S. Pat. No. 4,737,593 (Ellrich et al.), the content of which is herewith incorporated by reference.

Preferred acylphosphine oxides are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms. In particular, 2,4,6-trimethylbenzoyl diphenyl phosphine oxide was found to be useful (Lucirin™ TPO, BASF).

More specific examples include: bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-ethoxyphenyl-phosphine oxide, bis-(2,6-dichlorobenzoyl)-4-biphenylylphosphine oxide, bis-(2,6-dichlorobenzoyl)-4-propylphenylphosphine oxide, bis-(2,6-dichlorobenzoyl)-2-naphthylphosphine oxide, bis-(2,6-dichlorobenzoyl)-1-napthylphosphine oxide, bis-(2,6-dichlorobenzoyl)-4-chlorophenylphosphine oxide, bis-(2,6-dichlorobenzoyl)-2,4-dimethoxyphenylphosphine oxide, bis-(2,6-dichlorobenzoyl)decylphosphine oxide, bis-(2,6-dichlorobenzoyl)-4-octylphenylphosphine oxide, bis-(2,6-dimethoxybenzoyl)-2,5-dimethylphenylphosphine oxide, bis-(2,6-dimethoxybenzoyl)phenyl-phosphine oxide, bis-(2,4,6-trimethylbenzoyl)-2,5-dimethylphenylphosphine oxide, bis-(2,6-dichloro-3,4,5-trimethoxybenzoyl)-2,5-dimethylphenylphosphine oxide, bis-(2,6-dichloro-3,4,5-trimethoxybenzoyl)-4-ethoxyphenylphosphine oxide, bis-(2-methyl-1-naphthoyl)-2,5-dimethylphenyl-phosphine oxide, bis-(2-methyl-1-naphthoyl)phenylphosphine oxide, bis-(2-methyl-1-naphthoyl)-4-biphenylylphosphine oxide, bis-(2-methyl-1-naphthoyl)-4-ethoxyphenylphosphine oxide, bis-(2-methyl-1-naphthoyl)-2-naphthylphosphine oxide, bis-(2-methyl-1-naphthoyl)-4-propylphenylphosphine oxide, bis-(2-methyl-1-naphthoyl)-2,5-dimethylphosphine oxide, bis-(2-methoxy-1-naphthoyl)-4-ethoxyphenylphosphine oxide, bis-(2-methoxy-1-naphthoyl)-4-biphenylylphosphine oxide, bis-(2-methoxy-1-naphthoyl)-2-naphthylphosphine oxide and bis-(2-chloro-1-naphthoyl)-2,5-dimethylphenylphosphine oxide.

The acylphosphine oxide bis(2,4,6-trimethylbenzoyl)phenyl phosphine oxide (previously known as IRGACURE™ 819, Ciba Specialty Chemicals) is sometimes preferred.

A photo-initiator may be present in the following amounts: at least 0 or 0.005 or 0.01 wt. %; utmost 2 or 1.5 or 1 wt. %; range: 0.001 to 4 or 0.005 to 3 or 0.01 to 2 wt. %; wt. % with respect of the weight of the curable composition to be cured.

The initiator system described in the present text is in particular useful for curing a curable composition comprising curable components comprising acidic moieties, including resin-modified glass ionomer cements.

The initiator system can also be used for increasing the bond strength of a dental composition, in particular the dental composition described in the present text to hard dental tissue, in particular to dentin. A typical dental composition comprises polymerizable components, filler and additive(s).

The invention also relates to a curable dental composition comprising the initiator system described in the present text.

The dental composition can typically be characterized by the following properties alone or in combination:
a) viscosity: 10 to 5,000 Pa*s at 28° C., 100 to 2,000 Pa*s at 28° C., measured in oscillation at a frequency of 1.25 Hz and deflection of 1.75% 60 s after starting to mix the composition;
b) pH value: 1 to 6; e.g. if determined with a wet pH-sensitive indicator paper or stick;
c) shear bond strength to dentin: 1 to 10 MPa;
d) setting time: within 10 min measured at 28° C.

The combination of the following properties is sometimes preferred: a) and b); a) and c); b) and c).

The dental composition comprises polymerizable components, in particular curable components comprising acidic moieties. A polymerizable component comprises a component with at least one or two polymerizable moieties such as a (meth)acrylate moiety. The crosslinking or polymerization of the polymerizable component can be initiated by using a redox-initiator system.

In some embodiments the polymerizable components contain acidic groups or moieties.

The polymerizable components with acid moiety can typically be represented by the following formula $A_n BC_m$ with A being an ethylenically unsaturated group, such as a (meth)acryl moiety,
B being a spacer group, such as (i) linear or branched $C_1$ to $C_{12}$ alkyl, optionally substituted with other functional groups (e.g. halogenides (including Cl, Br, I), OH or mixtures thereof) (ii) $C_6$ to $C_{12}$ aryl, optionally substituted with other functional groups (e.g. halogenides, OH or mixtures thereof), (iii) organic group having 4 to 20 carbon atoms bonded to one another by one or more ether, thioether, ester, thioester, thiocarbonyl, amide, urethane, carbonyl and/or sulfonyl linkages, and
C being an acidic group, or precursor of an acidic group such as acid anhydride,
m, n being independently selected from 1, 2, 3, 4, 5 or 6,
wherein the acidic group comprises one or more carboxylic acid residues, such as —COOH or —CO—O—CO—, phosphoric acid residues, such as —O—P(O)(OH)OH, phosphonic acid residues, such as C—P(O)(OH)(OH), sulfonic acid residues, such as —SO$_3$H or sulfinic acid residues such as —SO$_2$H.

Examples of polymerizable components with acid moiety include, but are not limited to glycerol phosphate mono (meth)acrylate, glycerol phosphate di(meth)acrylate, hydroxyethyl (meth)acrylate (e.g., HEMA) phosphate, bis((meth)acryloxyethyl) phosphate, (meth)acryloxypropyl phosphate, bis((meth)-acryloxypropyl) phosphate, bis ((meth)acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di- or tri-methacrylate. Derivatives of these hardenable components bearing an acid moiety that can readily react e.g. with water to form the specific examples mentioned above, like acid halides or anhydrides are also contemplated.

If polymerizable components with acidic groups are present, they are typically present in the following amounts: at least 1 or 2 or 3 wt. %; utmost 25 or 20 or 15 wt. %; range: 1 to 25 or 2 to 20 or 3 to 15 wt. %; wt. % with respect of the weight of the composition.

In some embodiments the polymerizable components does not contain acidic groups. The polymerizable component without an acidic moiety is typically a free-radically polymerizable material, including ethylenically unsaturated monomer, monomers or oligomers or polymers. Suitable polymerizable component(s) without acidic moiety(s) can be characterized by the following formula:

$A_n BA_m$ with A being an ethylenically unsaturated group, such as a (meth)acryl moiety,
B being selected from (i) linear or branched $C_1$ to $C_{12}$ alkyl, optionally substituted with other functional groups (e.g. halogenides (including Cl, Br, I), OH or mixtures thereof) (ii) $C_6$ to $C_{12}$ aryl, optionally substituted with other functional groups (e.g. halogenides, OH or mixtures thereof), or (iii) organic group having 4 to 20 carbon atoms bonded to one another by one or more ether, thioether, ester, thioester, thiocarbonyl, amide, urethane, carbonyl and/or sulfonyl linkages,
m, n being independently selected from 0, 1, 2, 3, 4, 5 or 6 with the proviso that n+m is greater 0, that is that at least one A group is present.

Such polymerizable materials include mono-, di- or polyacrylates and methacrylates such as methyl acrylate, methyl methacrylate, ethyl (meth)acrylate, isopropyl (meth)acrylate, n-hexyl (meth)acrylate, stearyl (meth)acrylate, allyl (meth)acrylate, glycerol di(meth)acrylate, the diurethane dimethacrylate called UDMA (mixture of isomers, e.g. Röhm Plex 6661-0) being the reaction product of 2-hydroxyethyl methacrylate (HEMA) and 2,2,4-trimethylhexamethylene diisocyanate (TMDI), glycerol tri(meth)acrylate, ethyleneglycol di(meth)acrylate, diethyleneglycol di(meth)acrylate, triethyleneglycol di(meth)acrylate, 1,3-propanediol diacrylate, 1,3-propanediol dimethacrylate, trimethylolpropane tri(meth)acrylate, 1,2,4-butanetriol tri(meth)acrylate, 1,4-cyclohexanediol di(meth)acrylate, pentaerythritol tri(meth)acrylate, pentaerythritol tetraacrylate, pentaerythritol tetramethacrylate, sorbitol hexa(meth)acrylate, bis[1-(2-(meth)acryloxy)]-p-ethoxyphenyldimethylmethane, bis[1-(3-methacryloxy-2-hydroxy)]-p-propoxyphenyldimethylmethane (BisGMA), bis[1-(3-acryloxy-2-hydroxy)]-p-propoxy-phenyldimethylmethane and trishydroxyethyl-isocyanurate trimethacrylate; the bis-acrylates and bis-methacrylates of polyethylene glycols of molecular weight 200-500, copolymerizable mixtures of acrylated monomers (see e.g. U.S. Pat. No. 4,652,274), and acrylated oligomers (see e.g. U.S. Pat. No. 4,642,126); and vinyl compounds such as styrene, diallyl phthalate, divinyl succinate, divinyl adipate and divinylphthalate; polyfunctional (meth)acrylates comprising urethane, urea or amide groups. Mixtures of two or more of these free radically polymerizable materials can be used if desired.

Further polymerizable components which may be present include di(meth)acrylates of ethoxylated bis-phenol A, for example 2,2'-bis(4-(meth)acryloxytetraethoxyphenyl)propanes, urethane (meth)acrylates and (meth)acrylamides. The monomers used can furthermore be esters of [alpha]-cyanoacrylic acid, crotonic acid, cinnamic acid and sorbic acid.

It is also possible to use the methacrylic esters mentioned in EP 0 235 826, such as bis[3[4]-methacryl-oxymethyl-8 (9)-tricyclo[$5.2.1.0^{2,6}$]decylmethyl thioglycolate. Suitable are also 2,2-bis-4-(3-methacryloxy-2-hydroxypropoxy)phenylpropane (Bis-GMA), 2,2-bis-4-(3-methacryloxypropoxy) phenyl-propane, 7,7,9-trimethyl-4,13-dioxo-3,14-dioxa-5, 12-diazahexadecane-1,16-dioxy dimethacrylate (UDMA), urethane (meth)acrylates and di(meth)acrylates of bishydroxymethyltricyclo-($5.2.1.0^{2,6}$)decane.

These ethylenically unsaturated monomers can be employed in the dental composition(s) either alone or in combination with the other ethylenically unsaturated monomers. In addition or besides those components, other hardenable components which can be added include oligomeric or polymeric compounds, such as polyester (meth)acrylates, polyether (meth)acrylates, polycarbonate (meth)acrylates and polyurethane (meth)acrylates. The molecular weight of these compounds is typically less than 20,000 g/mol, particularly less than 15,000 g/mol and in particular less than 10,000 g/mol.

If polymerizable components without acidic groups are present, they are typically present in the following amounts: at least 1 or 10 or 15 wt. %; utmost 65 or 50 or 40 wt. %; range: 1 to 65 or 10 to 50 or 15 to 40 wt. %; wt. % with respect of the weight of the composition.

The dental composition may comprise curable components not comprising acidic moieties and curable components comprising acidic moieties.

The dental composition may also comprise one or more fillers. The fillers may be acid-reactive fillers or non acid-reactive fillers.

The composition may comprise one or more acid-reactive fillers.

If acid-reactive filler(s) and polyacids are present, the composition would be able to undergo a so-called glass-ionomer cement reaction.

According to one embodiment, the acid-reactive filler can be characterized by the following features alone or in combination:
a) Mean particle size: 1 to 25 μm;
b) (d10/μm): 0.5 μm to 3 μm; (d50/μm): 2 μm to 7 μm; (d90/μm): 6 μm to 30 μm;
c) pH value of a dispersion of 1 g filler stirred in 10 ml de-ionized water (having a pH of about 5) for 5 minutes: between 5 and 10.

The combination of features a) and b) or a) and c) can be preferred.

If the mean particle size of the acid-reactive filler is above the range outlined above, the consistency of the composition obtained when mixing the compositions contained in the parts of the kit of parts described in the present text might not be adequate and the desired mechanical properties might be negatively affected.

If the mean particle size of the acid-reactive filler is below the range outlined above, the setting time might be too fast.

Suitable acid-reactive fillers include metal oxides, metal hydroxides, hydroxyapatite, acid-reactive glasses including aluminosilicate glasses and fluoro aluminosilicate glasses.

Typical metal oxides include barium oxide, strontium oxide, calcium oxide, magnesium oxide, zinc oxide.

Typical metal hydroxides include calcium hydroxide, magnesium hydroxide, strontium hydroxide and mixtures thereof.

Typical acid-reactive glasses include aluminosilicate glasses and in particular, fluoro alumina-silicate ("FAS") glasses.

The glass can be made from a melt containing fluoride, silica, alumina, and other glass-forming ingredients using techniques familiar to those skilled in the FAS glassmaking art.

The FAS glass typically is in the form of particles that are sufficiently finely divided so that they can conveniently be mixed with the other cement components and will perform well when the resulting mixture is used in the mouth.

Suitable FAS glasses are familiar to those skilled in the art, and are available from a wide variety of commercial sources, and many are found in currently available glass ionomer cements such as those commercially available under the trade designations Ketac™-Molar or Ketac™-Fil Plus (3M Oral Care), and FUJI™ IX (GC).

Useful acid-reactive glasses can also be characterized by the Si/Al ratio. Fillers having a Si/Al ratio (by wt. %) of below 1.5 or 1.4 or 1.3 were found to be particularly useful.

Suitable acid-reactive fillers are also commercially available from e.g. Schott AG (Germany) or Specialty Glass (US).

If the amount of the acid-reactive filler is too high, mixing of the pastes of the kit of parts described in the present text might become more difficult. Furthermore, obtaining an adequate consistency and acceptable mechanical properties of the resulting composition might become difficult, as well.

If the amount of the acid-reactive filler is too low, formulating a suitable paste might become more difficult. Furthermore, the mechanical properties might become inferior.

The acid-reactive filler is typically present in the following amounts: at least 5 or 8 or 10 wt. %; utmost 70 or 60 or 50 wt. %; range: 5 to 70 or 8 to 60 or 10 to 50 wt. %; wt. % with respect of the weight of the whole composition. A range of 5 to 50 wt. % is sometimes preferred.

The non-acid reactive filler is preferably an inorganic filler.

Examples of suitable non acid-reactive fillers are naturally occurring or synthetic materials including, but not limited to: kaolin; silica particles (e.g., submicron pyrogenic silicas such as those available under the trade designations "AEROSIL™", including "OX 50," "130," "150" and "200", silicas from Evonic, and HDK™, including "H15", "H20", "H2000" from Wacker, and CAB-O-SIL M5 silica from Cabot Corp.), alumina, titania and zirconia particles.

Mixtures of these non-acid-reactive fillers are also contemplated.

Sometimes, the non acid-reactive filler is provided as a dispersion or sol of particles in a liquid (e.g. water).

If the filler is provided as an aqueous dispersion or sol, the amount of water in the aqueous dispersion or sol has to be taken into account when the amount of water and filler in the composition is calculated or determined.

Suitable non acid-reactive fillers are also commercially available as aqueous dispersions from e.g. Obermeier, Bad Berleburg, Germany under the trade name Levasil™, including type "50/50%", wherein the % value indicates the filler content in wt. %.

If desired, the surface of the particles of the non acid-reactive fillers can be surface treated. Suitable surface-treating agents include silanes, e.g. trimethoxysilanes carrying an organic functional group to modify the chemical properties of the particles. Suitable silanes are e.g. silanes to modify the acidic properties (carrying amino groups or carrying carboxylic acid groups) or silanes to modify the hydrophobicity/hydrophilicity (carrying an alkane chain or carrying a polyethylene glycol chain).

According to one embodiment, the non acid-reactive filler is selected from silica, (alumo)silicates, alumina and mixtures thereof.

The non acid-reactive filler is typically present in the following amounts: at least 0 or 4 or 6 wt. %; utmost 40 or 35 or 30 wt. %; range: 0 to 40 or 4 to 35 or 6 to 30 wt. %; wt. % with respect of the weight of the whole composition.

The dental composition may also comprise water. Typically, de-ionised water is used.

If the amount of the water is too low, obtaining a workable consistency of the obtained paste might become difficult.

If the amount of water is too high, obtaining a workable consistency of the obtained paste might become difficult, too. Furthermore, it will become difficult to achieve the desired mechanical properties and the paste might separate during storage.

If water is present, it is typically present in the following amounts: at least 0.25 or 0.5 or 1 wt. %; utmost 20 or 15 or 10 wt. %; range: 0.25 to 20 or 0.5 to 15 or 1 to 10 wt. %; wt. % with respect of the weight of the whole composition.

The composition may also comprise polyacrylic acid.

The polyacid should have a molecular weight sufficient to provide good storage, handling, and mixing properties, as well as to yield good material properties in the glass ionomer material.

According to one embodiment, the polyacid can be characterized by the following features alone or in combination: being a solid (at 23° C.); molecular weight (Mw): 2,000 to 250,000 or 4,000 to 100,000 g/mol (evaluated against a polyacrylic acid sodium salt standard using gel permeation chromatography).

If the molecular weight of the polyacid is too high, obtaining a workable consistency of the obtained paste when mixing the compositions contained in the kit of parts described in the present text might become difficult. Furthermore, preparation of the compositions might become difficult, too. In addition, the obtained mixture or composition might become too sticky (i.e. adheres to the dental instrument used for application).

If the molecular weight of the polyacid is too low, the viscosity of the obtained paste might become too low and the mechanical properties inferior.

Typically, the polyacid is a polymer having a plurality of acidic repeating units.

The polyacid to be used for the cement composition described in the present text is substantially free of polymerizable groups.

The polyacid need not be entirely water soluble, but typically it is at least sufficiently water-miscible so that it does not undergo substantial sedimentation when combined with other aqueous components.

The polyacid is hardenable in the presence of, for example, an acid-reactive filler and water, but does not contain ethylenically unsaturated groups.

That is, the polyacid is a polymer obtained by polymerising an unsaturated acid. However, due to the production process, a polyacid might still contain unavoidable traces of free monomers (e.g. up to 1 or 0.5 or 0.3 wt. % with respect to the amount of monomers used).

Typically, the unsaturated acid is an oxyacid (i.e., an oxygen containing acid) of carbon, sulfur, phosphorous, or boron. More typically, it is an oxyacid of carbon.

Suitable polyacids include, for example, polyalkenoic acids such as homopolymers and copolymers of unsaturated mono-, di-, or tricarboxylic acids.

Polyalkenoic acids can be prepared by the homopolymerization and copolymerization of unsaturated aliphatic carboxylic acids, e.g., acrylic acid, methacrylic acid, itaconic acid, maleic acid, glutaconic acid, aconitic acid, citraconic acid, mesaconic acid, fumaric acid, and tiglic acid.

Suitable polyacids also include alternating copolymers of maleic acid and ethylene (e.g. in a molar one to one ratio).

Suitable polyacids are also described in the following documents: U.S. Pat. No. 4,209,434 (Wilson et al.), U.S. Pat. No. 4,360,605 (Schmitt et al.). The content of these documents with respect to the description of the polyacid is herewith incorporated by reference.

Suitable polyacids are also included as aqueous solutions in the liquid component of commercially available products from e.g. 3M Oral Care (e.g. Ketac™ Fil Plus Handmix) or GC (e.g. Fuji™ IX GP Handmix).

The amount of polyacid should be sufficient to react with the acid-reactive filler and to provide an ionomer composition with desirable hardening properties.

If the amount of polyacid is too high, obtaining a workable consistency of the obtained paste when mixing the compositions contained in the kit of parts described in the present text might become difficult. Furthermore, preparation of the compositions might become difficult. In addition, the obtained mixture or composition might become too sticky (i.e. adheres to the dental instrument used for application).

If polyacid is present, it is typically present in the following amounts: at least 1 or 4 or 6 wt. %; utmost 25 or 20 or 15 wt. %; range: 1 to 25 or 4 to 20 or 6 to 15 wt. %; wt. % with respect of the weight of the whole composition. A range of 0.25 to 20 wt. % is sometimes preferred.

The composition can also comprise additives.

Additives which can be added include dyes, pigments, photo-bleachable colorants, plasticizsers, retarders and mixtures thereof.

Examples of dyes or pigments, which can be used include titanium dioxide or zinc sulphide (lithopones), red iron oxide 3395, Bayferrox™ 920 Z Yellow, Neazopon™ Blue 807 (copper phthalocyanine-based dye) or Helio™ Fast Yellow ER. These additives may be used for individual colouring of the dental compositions.

Examples of photo-bleachable colorants which can be present include Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. Further examples of photo-bleachable colorants can be found in U.S. Pat. No. 6,444,725.

Further additives, which can be added, include retarder(s), (such as 1,2-diphenylethylene), and plasticizers (including polyethylene glycol derivatives, polypropylene glycols, low-molecular-weight polyesters, dibutyl, dioctyl, dinonyl and diphenyl phthalate, di(isononyl adipate), tricresyl phosphate, paraffin oils, glycerol triacetate, bisphenol A diacetate, ethoxylated bisphenol A diacetate, and silicone oils).

There is no need for additives to be present, so additives might not be present at all. However, if they are present, they are typically present in an amount which is not detrimental to the intended purpose.

Additives are typically present in the following amounts: at least 0 or 0.01 wt. %; utmost 15 or 10 or 5 wt. %; range: 0 to 15 or 0 to 10 or 0.01 to 5 wt. %; wt. % with respect of the weight of the whole composition.

All components used in the dental composition and the initiator system described in the present text should be sufficiently biocompatible, that is, the composition should not produce a toxic, injurious, or immunological response in living tissue.

The initiator system and the dental composition typically do not comprise or is essentially free of the following components alone or in combination: persulfates in an amount of more than 0.1 wt. %; sulfinates in an amount of more than 0.1 wt. %; wt. % with respect to the weight of the composition.

According to certain embodiments, the dental composition is essentially free of either of these components alone or in combination.

In certain embodiments the dental composition may comprise, essentially consists of or consists of the respective components in the following amounts:
  initiator system described in the present text (comprising hydroperoxide, thiourea component and transition metal component): 0.1 to 5 wt. %,
  polymerizable components with acidic moiety: 0.5 to 15 wt. %,
  polymerizable components without acidic moiety: 1 to 50 wt. %,
  acid-reactive filler: 5 to 70 wt. %,
  non acid-reactive filler: 0 to 40 wt. %,
  polyacid: 1 to 25 wt. %,
  water: 0.25 to 20 wt. %,
  photo-initiator: 0 to 2 wt. %,
  additives: 0 to 15 wt. %,
wt. % with respect of the weight of the whole composition.

In certain embodiments the dental composition may comprise, essentially consists of or consists of the respective components in the following amounts:
  initiator system described in the present text (comprising hydroperoxide, thiourea component and
  transition metal component): 0.3 to 5 wt. %,
  polymerizable components with acidic moiety: 1 to 10 wt. %,
  polymerizable components without acidic moiety: 5 to 40 wt. %,
  acid-reactive filler: 5 to 50 wt. %,
  non acid-reactive filler: 4 to 35 wt. %,
  polyacid: 4 to 20 wt. %,
  water: 0.5 to 15 wt. %,
  photo-initiator: 0.01 to 1 wt. %,
  additives: 0 to 10 wt. %.
wt. % with respect of the weight of the whole composition.

The dental composition is typically provided as a kit of parts comprising an acid part or paste and a non-acidic part or paste.

The acidic part and non-acidic part are typically provided in a ratio of 3:1 to 1:3 or 2:1 to 1:2 with respect to volume, preferably in a ratio of 1:1 with respect to volume.

The components of the kit of parts are typically provided in a form avoiding an undesired reaction or interaction among them.

The acidic part or paste typically comprises, essentially consists of or consists of
  polymerizable components with acidic moiety, preferably in an amount of 1 to 20 wt. %,
  optionally polymerizable components without acidic moiety, preferably in an amount of 0 to 50 or 5 to 40 wt. %,
  hydroperoxide component, preferably in an amount of 0.1 to 5 wt. %,
  optionally transition metal component, preferably in an amount of 0 to 0.5 or 0.001 to 0.5,
  polyacid, preferably in an amount of 1 to 30 wt. %,
  optionally non acid-reactive filler, preferably in an amount of 0 to 50 or 5 to 50 wt. %,
  water, preferably in an amount of 0.5 to 20 or 1 to 20 wt. %,
  optionally additive(s) in an amount of 0 to 10 wt. %,
  wt. % with respect to the amount of the acidic part or paste.

The non-acidic part or paste typically comprises, essentially consists of or consists of
  polymerizable components without acidic moiety, preferably in an amount of 1 to 60 wt. % or 5 to 40 wt. %,
  optionally a photo-initiator, preferably in an amount of 0 to 2 wt. % or 0.01 to 2 wt. %,
  polymerizable thiourea component, preferably in an amount of 0.1 to 3 wt. %,
  acid-reactive filler, preferably in an amount of 15 to 70 wt. %,
  optionally non-acid-reactive filler, preferably in an amount of 0 to 30 or 1 to 20 wt. %,
  optionally additive(s), preferably in an amount of 0 to 10 wt. %,
  wt. % with respect to the amount of the non-acidic part or paste.

The viscosity of the individual parts or pastes is typically in a range of 5 to 1,000 Pa*s at 23° C., or 10 to 500 Pa*s at 23° C., measured at a shear rate of 20 $s^{-1}$.

The initiator system described in the present text can be produced by mixing the respective components. If desired, a speed-mixer or kneading machine can be used. As appropriate the production is done under save-light conditions.

The present invention is also directed to a kit of parts.

The kit of parts may comprise the dental composition described in the present text and the following components alone or in combination: dental milling block; dental crown; mixing tips; dental adhesive or bonding system; conditioning liquid for crown material or tooth material.

Suitable dental milling blocks typically comprise a porous zirconia material, which contains yttria as a phase-stabilizing component and colouring components. Examples of dental milling blocks are described in US2017/020639 (Jahns et al.), US2015/238291A1 (Hauptmann et al.).

Prefabricated dental crowns which can be used include stainless steel crowns (3M Oral Care) or plastic crowns made out of polyacetal, polyacrylate, polymethacrylate (PMMA), polyaryletherketone (PAEK), polyetherketon (PEK), polyetheretherketon (PEEK), polyetherimide (PEI), polyethersulfone (PES) and polysulfone (PSU).

Suitable prefabricated dental crown are also described in U.S. Pat. No. 8,651,867B2 (Zilberman), WO2007/098485A2 (Nusmile), WO2008/033758A2 (3M), and US2007/0196792A1 (Johnson et al.). The content of the above mentioned references is herewith incorporated by reference.

Commercially available dental adhesives or bonding systems which can be used include Scotchbond™ Universal Adhesive (3M Oral Care), Scotchbond™ Universal Plus Adhesive (3M Oral Care).

Commercially available conditioners which can be used include Ketac™ Conditioner (3M Oral Care) and Cavity Conditioner (GC).

The dental composition described in the present text is typically stored in an adequate packaging material or device.

If the dental composition is provided as a kit of parts comprising an acidic paste and a non-acidic paste, the pastes may be contained in separate sealable vessels or receptacles (e.g. made out of plastic or glass).

For use, the practitioner may take adequate portions of the compositions contained from the vessels and mix the portions by hand on a mixing plate.

According to a preferred embodiment, the acidic paste and the non-acidic paste are contained in separate compartments of a storing device.

The storing device typically comprises two compartments for storing the respective parts, each compartment being equipped with a nozzle for delivering the respective part. Once delivered in adequate portions, the parts can then be mixed by hand on a mixing plate. Suitable storing devices include cartridges, syringes and tubes.

According to another embodiment, the storing device has an interface for receiving a static mixing tip. The mixing tip is used for mixing the respective pastes. Static mixing tips are commercially available e.g. from SulzerMixpac company.

The storing device typically comprises two housings or compartments having a front end with a nozzle and a rear end and at least one piston movable in the housing or compartment.

Cartridges which can be used are described e.g. in US2007/0090079A1 (Keller) or U.S. Pat. No. 5,918,772 (Keller et al.), the disclosure of which is incorporated by reference. Some of the cartridges which can be used are commercially available e.g. from Sulzer Mixpac AG (Switzerland). Static mixing tips which can be used are described e.g. in US2006/0187752A1 (Keller) or in U.S. Pat. No. 5,944,419 (Streiff), the disclosure of which is incorporated by reference. Mixing tips which can be used are commercially available from Sulzer Mixpac AG (Switzerland), as well.

Other suitable storing devices are described e.g. in WO2010/123800 (3M), WO2005/016783 (3M), WO2007/104037 (3M), WO2009/061884 (3M), in particular the device shown in FIG. 14 of WO2009/061884 (3M) or WO2015/073246 (3M), in particular the device shown in FIG. 1 of WO2015/07346. Those storing devices have the shape of a syringe. The content of these references is herewith incorporated by reference, as well.

Alternatively, but less preferred, paste/paste compositions described in the present text can be provided in two individual syringes and the individual pastes can be mixed by hand prior to use.

Thus, the invention is also directed to a device for storing the kit of parts described in the present text, the device comprising two compartments, Compartment A and Compartment B, Compartment A containing the acidic paste and Compartment B containing the non-acidic paste, the acidic paste and the non-acidic paste being as described in the present text, Compartment A and Compartment B both comprising a nozzle or an interface for receiving an entrance orifice of a static mixing tip.

The dental composition described in the present text can be used as dental cement for fixing a dental restoration to the surface of a prepared tooth. The dental restoration typically has the shape of a dental crown or bridge, veneer, onlay or inlay.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention. Unless otherwise indicated, all parts and percentages are by weight.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

Methods

Viscosity of Single Parts

If desired, the viscosity of the single parts/pastes of the composition can be measured using a Physica MCR 301 Rheometer (Anton Paar, Graz, Austria) with a plate/plate geometry under controlled shear rate at 23° C. The plate diameter is 15 mm, the separation gap between the plates 0.5 mm. The shear rate is 20 s$^{-1}$.

Viscosity of Two-Part Composition

If desired, the viscosity of the two-part composition can be measured using a Physica MCR 301 Rheometer (Anton Paar, Graz, Austria) with a plate/plate geometry under controlled oscillation at 28° C. The plate diameter is 8 mm, the separation gap between the plates 0.75 mm. The oscillation frequency is 1.25 Hz and deflection is 1.75%.

Particle Size (Suitable for Micro-Sized Particles)

If desired, the particle size distribution including the particle size (d50) per volume can be determined by laser diffraction with a Mastersizer 2000 (Malvern) particle size detection device applying the Fraunhofer approximation. During the measurement, ultrasonic is typically used to accurately disperse the sample. For water-insoluble particles, water is typically used as dispersant.

Particle Size (Suitable for Nano-Sized Particles)

If desired, particle size measurements can made using a light scattering particle sizer equipped with a red laser having a 633 nm wavelength of light (obtained under the trade designation "ZETA SIZER—Nano Series, Model ZEN3600" from Malvern Instruments Inc., Westborough, MA). Each sample is analyzed in a one-centimeter square polystyrene sample cuvette. The sample is diluted 1:100, e.g. 1 g of sample is given to 100 g of de-ionized water and mixed. The sample cuvette is filled with about 1 gram of diluted sample. The sample cuvette is then placed in the instrument and equilibrated at 25° C. The instrument parameters are set as follows: dispersant refractive index 1.330, dispersant viscosity 0.8872 mPa*s, material refractive index 1.43, and material absorption value 0.00 units. The automatic size-measurement procedure is then run. The instrument automatically adjusts the laser-beam position and attenuator setting to obtain the best measurement of particle size.

The light scattering particle-sizer illuminates the sample with a laser and analyzes the intensity fluctuations of the light scattered from the particles at an angle of 173 degrees. The method of Photon Correlation Spectroscopy (PCS) can be used by the instrument to calculate the particle size. PCS uses the fluctuating light intensity to measure Brownian motion of the particles in the liquid. The particle size is then calculated to be the diameter of sphere that moves at the measured speed.

The intensity of the light scattered by the particle is proportional to the sixth power of the particle diameter. The Z-average size or cumulant mean is a mean calculated from the intensity distribution and the calculation is based on assumptions that the particles are mono-modal, mono-disperse, and spherical. Related functions calculated from the fluctuating light intensity are the Intensity Distribution and its mean. The mean of the Intensity Distribution is calculated based on the assumption that the particles are spherical. Both the Z-average size and the Intensity Distribution mean are more sensitive to larger particles than smaller ones.

The Volume Distribution gives the percentage of the total volume of particles corresponding to particles in a given size range. The volume-average size is the size of a particle that corresponds to the mean of the Volume Distribution. Since the volume of a particle is proportional to the third power of the diameter, this distribution is less sensitive to larger particles than the Z-average size. Thus, the volume-average will typically be a smaller value than the Z-average size. In the scope of this document the Z-average size is referred to as "mean particle size".

pH Value

If desired, the pH value of can be determined as follows: a wet pH sensitive paper or test stick is brought in contact with the composition to be analysed.

Setting Time

If desired, the setting time can be determined by recording the viscosity of the mixed composition during curing over a certain time period. Viscosity is measured using a Physica MCR 301 Rheometer (Anton Paar, Graz, Austria) with a plate/plate geometry at 28° C. From the recorded graph 2 measuring points are taken, which show the beginning and the end of curing. The two measuring points are: a) Beginning of curing=Time when viscosity is three times the starting viscosity, which is determined 60 s after start of mixing, b) Setting Time=Time when shear stress reaches 100,000 Pa.

Shear Bond Strength (SBS)

Bovine teeth were ground flat to expose dentin, polished (grit 320 sandpaper), water-rinsed, and gently air-dried. Sandblasted and salinized steel rods (diameter=4 mm) were cemented onto the prepared teeth using a mixture of the pastes to be examined. A load of 20 g/mm$^2$ was put onto the cemented rods for 10 min at 36° C. and then removed. After that the specimens were stored for 22 h. Then, specimens were subjected to shear bond strength (SBS) testing using a Zwick 010 (Germany) tensile testing machine (speed=0.75 mm/min).

Water Contact Angel

If desired, the water contact angel can be determined as follows: a drop of a 10 wt. % ethanolic solution of the component to be tested is applied onto the surface of a dental mixing pad. The ethanolic solvent is evaporated to obtain a coated surface (approx. size: 4 cm$^2$). On that surface a drop of water is placed and the development of the water-contact angle is analysed at 23° C. (Kruess Advance Software 1.13.1.31401). The average value obtained within 0 to 12 s after placement of the drop is taken.

TABLE 1

| Materials | | |
| --- | --- | --- |
| Compound | Abbreviation | Description |
| Hydroxy ethyl methacrylate | HEMA | Monomer |
| Glycerine-1,3-dimethacrylate | GDMA | Monomer |
| Glycerol dimethacrylate phosphate | GDMAP | Monomer |
| Water, de-ionized | Water | Water |
| Poly(acrylic acid-co-maleic acid) co-polymer (1:1 co-polymer), Mw = 20,000 g/mol | PAA | Polyacrylic acid |
| 10% 2,6-di-tert-butyl 4-hydroxy toluene in HEMA | Stabsol 1 | Stabilizer |
| 10% 4-Hydroxy-2,2,6,6-tetramethylpiperidine 1-oxyl (4-Hydroxy-TEMPO) in HEMA | Stabsol 2 | Stabilizer |
| N-(5-methacryloxypentyl)-N'-ethyl thiourea | MOPETU | Reductant |
| Dimethylthiourea | DMTU | Reductant |
| N-Allyl-N'-(2-(2-methacryloxyethyl)carbamatoethyl)thio urea (*) | SUMITU | Reductant |
| N-(11-Methacryloxyundecyl)-N'-ethylthiourea | MOUETU | Reductant |
| Tetramethylbutyl hydroperoxide | TMBH-L | Oxidant |
| 1% copper procetonate in HEMA | Cu-catalyst | Catalyst |
| 1% Irgacure 819 in GDMA | Photosol | Photo-initiator |
| Aerosil ® R805 | R805 | Non acid-reactive Filler |
| Aerosil ® OX50 | OX50 | Non acid-reactive Filler |
| FAS glass 0.3% silanized, <63 µm | FAS glass | Acid-reactive filler |
| Encapsulated CaO filler (**) | CaO-Encap | Ca-ions releasing component |
| YbF3, silane-treated, 100 nm | YbF3 | Radiopaque filler |

(*) according to example 14 of US2003/0166740A1;
(**) according to example 23 of WO2018/102484A1

General Process for Producing Pastes

The preparation of the pastes was conducted by mixing the given components under standardized conditions (room temperature, ambient pressure, 50% relative humidity) using a speedmixer.

TABLE 2

Aqueous, acidic pastes

| Compound | SF-S-200 Amount [wt. %] | SF-S-203 Amount [wt. %] | SF-S-266 Amount [wt. %] |
|---|---|---|---|
| HEMA | 30.03 | 29.57 | 29.78 |
| GDMAP | 9.55 | 9.55 | 9.55 |
| Water | 3.00 | 3.00 | 4.00 |
| PAA | 19.85 | 19.85 | 18.85 |
| Cu-catalyst | 0.63 | 0.63 | 0.60 |
| Stabsol 1 | 0.86 | 0.86 | 0.86 |
| TMBH-L | 0.94 | 1.40 | 1.22 |
| OX50 | 10.55 | 10.55 | 10.55 |
| YbF3 | 24.60 | 24.60 | 24.60 |

TABLE 3

Non-acidic pastes

| Compound | SF-G-206 Amount [wt. %] | SF-G-223 Amount [wt. %] | SF-G-293 Amount [wt. %] | SF-G-303 Amount [wt. %] |
|---|---|---|---|---|
| UDMA | 3.40 | 3.40 | 3.40 | 3.40 |
| GDMA | 24.80 | 24.27 | 24.65 | 25.37 |
| Photosol | 3.00 | 3.00 | 3.00 | 3.00 |
| Stabsol 2 | 0.10 | 0.10 | 0.10 | 0.10 |
| DMTU | 0.52 | — | — | — |
| MOPETU | — | 1.05 | 1.05 | — |
| SUMITU | — | — | — | 1.28 |
| R805 | 6.00 | 6.00 | 6.00 | 6.00 |
| FAS glass | 62.18 | 62.18 | 46.80 | 45.85 |
| CaO-Encap | — | — | 15.00 | 15.00 |

For obtaining adequate and comparable curing conditions, the amount of the polymerizable thiourea component was increased in the non-acidic paste so that the molar amount of the thiourea components in the respective pastes are essentially equal (DMTU: 104 g/mol; MOPETU: 258 g/mol).

The respective pastes were mixed in a ratio of 1 to 1.5 with respect to weight (corresponding to a ratio of about 1:1 with respect to volume).

TABLE 4

Comparative & inventive examples

| Example | SF-S-XXX | SF-G-XXX | SBS to Dentin [MPa] | Setting Time (min) |
|---|---|---|---|---|
| 1 (comparative) | SF-S-200 | SF-G-206 | 0.8 ± 0.2 | 5.1 |
| 2 (inventive) | SF-S-200 | SF-G-223 | 1.9 ± 1.0 | 7.1 |
| 3 (comparative) | SF-S-203 | SF-G-206 | 0.7 ± 0.4 | 3.6 |
| 4 (inventive) | SF-S-203 | SF-G-223 | 4.6 ± 2.0 | 4.9 |
| 5 (inventive) | SF-S-266 | SF-G-293 | 5.0 ± 1.8 | 4.4 |
| 6 (comparative) | SF-S-266 | SF-G-303 | 3.5 ± 1.7 | 5.9 |

TABLE 5

Water Contact Angle

| Substance | Water Contact Angle [°] |
|---|---|
| DMTU | 7.4 |
| MOPETU | 29.8 |
| SUMITU | 48.9 |
| MOUETU | 70.9 |

It was found that the addition of the polymerizable thiourea component of the invention to a curable composition, in particular to a resin-modified glass ionomer composition leads to an improved bond strength of the cured composition to dentin within a reasonable setting time.

This becomes clear if the shear bond strength values of Example 1 (comparative) and Example 2 (inventive) are compared. Example 2 shows higher shear bond strength.

As setting time is longer in Example 2, the composition was adjusted in Example 4 (inventive) by using a higher amount of hydroperoxide. This resulted in even a higher shear bond strength of Example 4 (inventive) and a much more pronounced difference to Example 3 (comparative).

Example 3 (comparative) shows that the higher bond strength of Example 4 is not related to the higher amount of hydroperoxide as the amount of hydroperoxide in Examples 3 and 4 is equal.

Example 5 (inventive) shows that the polymerizable thiourea component of the invention provides better shear bond strength to dentin than the polymerizable thiourea component as described in example 14 of US2003/0166740A1 (Example 6, comparative).

Further, it was found that the polymerizable thiourea component of the present invention shows a well-balanced hydrophilicity. The component is less hydrophilic than DMTU but provides enough hydrophilicity to improve shear bond strength to dentin. However, the water contact angle alone does not necessarily have a direct impact on the bond strength as Example 6 (using the component of example 14 of US2003/0166740A1) has a higher water contact angle but lower bond strength than the inventive polymerizable thiourea component (Example 5).

The invention claimed is:

1. An initiator system for curing a dental composition, the initiator system comprising
   a hydroperoxide component,
   a transition metal component comprising ions of Cu, Ti, V, Cr, Mn, Fe, Co, Ni, Zn or mixtures thereof,
   a polymerizable thiourea component, the polymerizable thiourea component comprising a thiourea moiety which is attached to a (meth)acrylate moiety through a $C_{3-11}$ alkyl chain and having the formula

MA-S-TU-R with
   MA: (meth)acrylate,
   S: $C_{3-11}$ alkyl,
   TU: NH—CS—NH
   R: $C_1$ to $C_6$ alkyl or cyclo alkyl.

2. The initiator system according to claim 1, the hydroperoxide component and polymerizable thiourea component being present in a molar ratio of 3/1 to 1/2 with respect to the ratio of hydroperoxide moiety and thiourea moiety.

3. The initiator system according to claim 1, the hydroperoxide component being selected from tetramethylbutyl hydroperoxide, t-butyl hydroperoxide, t-amyl hydroperoxide, cumene hydroperoxide, p-menthane hydroperoxide, p-isopropylcumyl hydro-peroxide, diisopropylbenzene hydroperoxide, and diisopropylbenzene dihydroperoxide, benzene hydroperoxide, pinane hydroperoxide, 5-phenyl-4-pentenylhydroperoxide, and mixtures thereof.

4. The initiator system according to claim 1, the polymerizable thiourea component having an average water-contact angle of more than 10° determined over a time period of 0 to 12 s at 23° C.

5. The initiator system according to claim 1, the polymerizable thiourea component being selected from N-(5-methacryloxypentyl)-N'-ethyl thiourea, N-(5-meth-acryloxypentyl)-N'-cyclohexyl thiourea, N-(5-methacryloxyundecyl)-N'-ethyl thiourea and mixtures thereof.

6. The initiator system according to claim 1, the transition metal component comprising copper acetate, copper chloride, copper benzoate, copper acetylacetonate, copper naphthenate, copper carboxylates, copper bis(1-phenylpentan-1,3-dione) complex, copper salicylate, complexes of copper with thiourea, ethylenediaminetetraacetic acid and/or mixtures thereof.

7. The initiator system according to claim 1 comprising in addition a photo-initiator.

8. The initiator system according to claim 1 comprising a stabilizer component(s) comprising a free-radical moiety.

9. The initiator system according to claim 8, the stabilizer(s) being selected from 2,2-diphenyl-1-picrylhydrazyl, 4-hydroxy-2,2,6,6-tetramethyl-piperidine 1-oxyl, 2,2,6,6-Tetramethyl-piperidinyloxyl, 2,6-di-tert-butyl-α-(3,5-di-tert-butyl-4-oxo-2,5-cyclohexadien-1-ylidene)-p-tolyloxyl, triphenylmethyl radical, 2,6-bis(1,1-dimethylethyl)-4-methylphenol and mixtures thereof.

10. A dental composition comprising
the initiator system according to claim 1,
polymerizable components comprising acidic moieties,
optionally filler(s),
optionally additive(s).

11. The dental composition according to claim 10 comprising
the initiator system in an amount of 0.1 to 5 wt. %,
polymerizable components comprising acidic moieties in an amount of 0.5 to 15 wt. %,
polymerizable components not comprising acidic moieties in an amount of 1 to 50 wt. %
water in an amount of 0.25 to 20 wt. %,
acid-reactive filler in an amount of 5 to 70 wt. %,
non acid-reactive filler in an amount of 0 to 40 wt. %,
polyacid in an amount of 1 to 25 wt. %,
additive(s) in an amount of 0 to 15 wt. %,
wt. % with respect to the dental composition.

12. The dental composition according to claim 1 provided as a two-part composition comprising an acidic part and a non-acidic part,
acidic part and non-acidic part being provided in a ratio of 3:1 to 1:3 with respect to volume,
the acidic part comprising
polymerizable components with acidic moiety,
optionally polymerizable components without acidic moiety,
the hydroperoxide component,
the transition metal component,
polyacid,
non acid-reactive filler,
water,
additive(s),
the non-acidic part comprising
polymerizable components without acidic moiety,
optionally a photo-initiator,
the polymerizable thiourea component,
acid-reactive filler,
non-acid-reactive filler,
additive(s).

13. A kit of parts comprising the dental composition according to claim 10 and the following parts alone or in combination: dental milling block; dental crown; mixing tips; dental adhesive; dental conditioner.

* * * * *